United States Patent [19]

Auerbach et al.

[11] 4,258,059
[45] Mar. 24, 1981

[54] AMINO-BENZAMIDES

[75] Inventors: Joseph Auerbach, Brooklyn; Martin L. Kantor, Mamaroneck, both of N.Y.

[73] Assignee: USV Pharmaceutical Corporation, Tuckahoe, N.Y.

[21] Appl. No.: 50,806

[22] Filed: Jun. 21, 1979

Related U.S. Application Data

[63] Continuation-in-part of Ser. No. 969,653, Dec. 15, 1978, abandoned.

[51] Int. Cl.³ .................... A61K 31/18; C07C 143/79
[52] U.S. Cl. ...................................... 424/321; 564/86; 564/149; 564/311
[58] Field of Search ..................... 260/556 C; 424/321

[56] References Cited

U.S. PATENT DOCUMENTS 3,119,847  7/1964  Jucker et al. ................. 260/556 C

FOREIGN PATENT DOCUMENTS 1430942 12/1964 France ................. 260/556 C
240572 11/1969 U.S.S.R. ................. 260/556 C

OTHER PUBLICATIONS

Jucker et al (IV), Helv. Chim. Acta, vol. 45, pp. 2316 to 2325 (1962).

Primary Examiner—John D. Randolph
Attorney, Agent, or Firm—Leon E. Tenenbaum

[57] ABSTRACT

Compounds of the formula

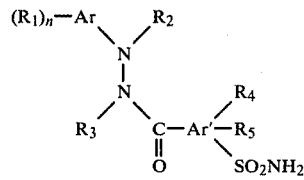

wherein:
Ar and Ar' are independently alicyclic aryl or heterocyclic aryl groups;
$R_1$ is a substituent replacing a hydrogen on the ring and is independently hydroxy, alkyl, alkoxy, halogen, nitro, amino, monoalkyl-amino, dialkyl-amino, sulfhydryl, alkylmercapto, sulfonamido, carboxy, carbalkoxy, or trihalomethyl;
n is an integer from 0 to 5 inclusive;
$R_2$ and $R_3$ are independently hydrogen, alkyl, alkenyl, alkynyl, cycloalkyl, cycloalkenyl, phenyl, or cycloalkyl-alkyl; and
$R_4$ and $R_5$ are independently halogen or trihalomethyl, with the proviso that when both Ar and Ar' are phenyl and n is 0, both $R_2$ and $R_3$ are not hydrogen.

9 Claims, No Drawings

AMINO-BENZAMIDES

This application is a continuation-in-part of patent application Ser. No. 969,653, filed Dec. 15, 1978, now abandoned.

This invention relates to new organic compounds having valuable pharmaceutical activity. It particularly relates to compounds having antihypertensive and diuretic activity and to a process for the preparation of said compounds.

The invention provides compounds of the formula

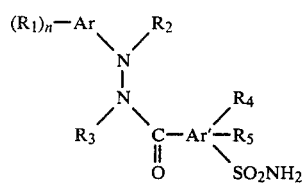

wherein:

Ar and Ar' are independently alicyclic aryl or heterocyclic aryl groups;

$R_1$ is a substituent replacing a hydrogen on the ring and is independently hydroxy, alkyl, alkoxy, halogen, nitro, amino, monoalkyl-amino, dialkyl-amino, sulfhydryl, alkylmercapto, sulfonamido, carboxy, carbalkoxy, or trihalomethyl;

n is an integer from 0 to 5 inclusive;

$R_2$ and $R_3$ are independently hydrogen, alkyl, alkenyl, alkynyl, cycloalkyl, cycloalkenyl, phenyl, or cycloalkyl-alkyl; and $R_4$ and $R_5$ are independently halogen or trihalomethyl, with the proviso that when both Ar and Ar' are phenyl and n is 0, both $R_2$ and $R_3$ are not hydrogen.

Preferably, the alkyl, alkenyl and alkynyl groups contain up to 6 carbon atoms and may be straight chained or branched, the cycloalkyl groups contain from 3 to 7 carbon atoms, and Ar' is phenyl.

In accordance with this invention the compounds are prepared by the reaction of a sulfamoyl chlorobenzoyl chloride of the formula

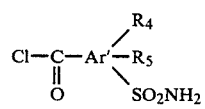

with a hydrazine of the formula

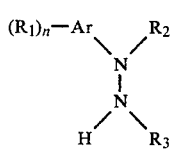

wherein $R_1$, $R_2$, $R_3$, $R_4$ and $R_5$ and Ar and n are the same as described above.

The hydrazines are readily prepared using standard methods by the nitrosation of an amine of the formula

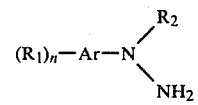

to form the nitrosamine

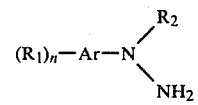

which is then reduced to the hydrazine of the formula $$(R_1)_n-Ar-N\begin{matrix}R_2\\NH_2\end{matrix}$$

The $R_3$ and

groups can then be introduced by standard methods.

Another process for preparing the compounds of the present invention consists in reacting a compound of the

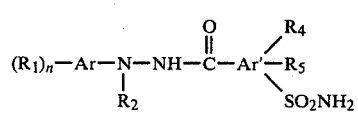

with a halide of the formula $$R_2-Hal$$

where Hal is a halogen, preferaby chlorine or bromine, to yield a compound of the formula $$(R_1)_n-Ar-N(R_2)-NH-\overset{O}{\overset{\|}{C}}-Ar'\begin{matrix}R_4\\R_5\\SO_2NH_2\end{matrix}$$

The invention will be more fully illustrated in the examples which follow. These examples are given by way of illustration and are not to be considered as limiting.

EXAMPLE 1

N-Nitroso-N-isopropylaniline

A mixture of 36 g (0.125 mol) N-isopropylaniline, 45 ml hydrochloric acid, and 100 g ice was maintained at 10° C. while a solution of 25 g (0.36 mol) sodium nitrite in 90 ml water was added over a 10 minute period. After the addition was completed, the mixture was allowed to stir for 1 hour. When stirring was discontinued an oily layer separated. The oil was removed and combined with subsequent toluene washing of the aqueous layer. The resultant toluene solution was dried over magnesium sulfate, filtered, and stripped of solvent under diminished pressure to yield the N-nitroso compound.

EXAMPLE 2

1-Isopropyl-1-phenyl-hydrazine hydrochloride

The N-nitroso compound of Example 1 was readily reduced by gradually adding a solution of 12.8 g (0.08 mol) of said compound in 100 ml glacial acetic acid to a vigorously stirred suspension of 25 g zinc dust in 35 ml water. Throughout this addition the temperature was maintained between 10° C. and 20° C. After the addition was completed, the mixture was stirred for 15 minutes at room temperature and was then warmed to 80° on a steam bath. Unreacted zinc was filtered from the hot reaction mixture and was washed with three 15 ml portions of warm 5% hydrochloric acid. The combined washings and filtrate was cooled, and the zinc hydroxide which precipitated was redissolved by the addition of 150 ml of 40% sodium hydroxide. The oily layer which separated was removed and combined with ethereal washings of the aqueous layer. This ethereal solution was dried over magnesium sulfate and filtered. Acidification with gaseous hydrochloric acid yielded the salt of the hydrazine which separated as an oil and was removed from the ethereal solution.

EXAMPLE 3

1-Isopropyl-1-phenyl-2-(3-sulfamoyl-4-chlorobenzoyl)-hydrazine

Neutralization of the hydrazine hydrochloride of Example 2 was effected by stirring with 19.6 g (0.21 mol) sodium bicarbonate in 100 ml isopropanol. When gas evolution ceased (1 ½ hours) the system was cooled in an ice-water bath, and 25 g (0.1 mol) 3-sulfamoyl-4-chlorobenzoyl chloride was added in several portions. Throughout this addition the temperature was maintained between 5° and 20° C. After the addition the reaction mixture was stirred at room temperature overnight. The reaction mixture was then cooled to 0°-5° C., diluted with 80 ml water, and stirred for 2 more hours. Solid material which precipitated was collected and was washed with three 40 ml portions of cold 60% isopropanol. Recrystallization from methylene chloride/ether yielded crystals, mp 112°-124°.

EXAMPLE 4

1-Phenyl-1-n-propyl-hydrazine

N-nitroso-N-propylaniline, prepared from N-n-propylaniline by the same method as described in Example 1, was conveniently reduced with lithium aluminum hydride (LAH). The LAH in 450 ml dry ether was heated under reflux for 15 minutes, and a solution of 32.8 g (0.2 mol) crude 4 in 250 ml dry ether was added dropwise. The reaction mixture was allowed to stir for 3 hours before it was quenched by the dropwise addition of 12 ml water and 14 ml 20% sodium hydroxide. The resultant suspension was filtered free of inorganic salts, dried and stripped of solvents under diminished pressure. Distillation of the residue yielded the desired compound bp 55°-57°/0.12 mm.

EXAMPLE 5

1-n-Propyl-1-phenyl-2-(3-sulfamoyl-4 chlorobenzoyl) hydrazine

A vigorously stirred mixture of 14.0 g (0.1 mol) 1-phenyl-1-n-propylhydrazine, 8.4 g (0.1 mol) sodium bicarbonate, and 100 ml isopropanol was chilled to 0°-5° C., 23 g (0.09 mol) 3-sulfamoyl-4-chlorobenzoyl chloride was added in one portion, and the reaction mixture was allowed to stir for several hours, gradually warming to room temperature. Dilution with water and refrigeration overnight yielded solid material which was collected and recrystallized from acetone/water, mp. 102° C. (d).

EXAMPLE 6

1-Cyclohexyl-1-phenyl-hydrazine

N-Cyclohexyl-N-nitrosoaniline, prepared from N-cyclohexylaniline by the method described in Example 1 was subsequently reduced to the hydrazine by the lithium aluminum hydride method described in Example 4. 1-Cyclohexyl-1-phenyl hydrazine distilled at 120°-150° C./0.2 mm.

EXAMPLE 7

1-Cyclohexyl-1-phenyl-2-(3-sulfamoyl-4-chlorobenzoyl)-hydrazine

A mixture of 8.5 g (0.045 mol) 1-cyclohexyl-1-phenyl hydrazine in 50 ml isopropanol and 4.7 g (0.045 mol) sodium bicarbonate was stirred and chilled. Addition of 11.36 g (0.045 mol) 3-sulfamoyl-4-chlorobenzoyl chloride was made in several portions. The mixture was stirred for 2 hours at room temperature and for 2.5 hours at 40°-50° C. Dilution of the reaction mixture with water yielded a solid material which was recrystallized from aqueous ethanol. M.P. 216°-217° C.

EXAMPLE 8

1-Phenyl-2-(3-sulfamoyl-4-chlorobenzoyl)-hydrazine

In a 1 liter round bottom flask were placed phenyl hydrazine (54.1 g, 0.5 mol), triethylamine (50.5 g, 0.5 mol), and 150 ml of 1,2 dimethoxyethane. Then the mixture was cooled to ice-bath temperature and with good stirring and over 10 minutes a solution of 3-sulfamoyl-4-chlorobenzoyl chloride 97.1% (61 g, 0.24 mol) in 150 ml 1,2 dimethoxyethane was added dropwise. The reaction was permitted to reach ambient temperature. After standing for 6 days the solvent was evaporated under vacuum and the residue taken up in 500 ml of ethyl acetate. The organic phase was washed twice with 2N H₂SO₄, with water and finally with 1 molar sodium bicarbonate solution. The ethyl acetate phase was separated and dried with magnesium sulfate, clarified and concentrated to crystallization. 35 g of product mp 189°-190° C. were obtained.

EXAMPLE 9

1-Allyl-1-phenyl-2-(3-sulfamoyl-4-chlorobenzoyl)-hydrazine

In a three necked 1 liter round bottom reaction vessel equipped with a mechanical stirrer and reflux condenser were placed 48.8 g (0.15 mol) of the compound of Example 8 and 125 ml of hexamethylphosphorictriamide. The mixture was heated with stirring under nitrogen to 80°-85° C. To this solution 126 g (1.5 mol) of sodium bicarbonate powder was added portionwise followed by 20 g (0.17 mol) of allyl bromide. After 2.25 hours an additional 1.8 g (0.015 mol) of allyl bromide was added. After 29 hours of heating the reaction mixture was cooled to room temperature diluted with 700 ml of ethyl acetate, and the slurry was cross washed with water and diluted brine. The ethyl acetate was separated, dried with magnesium sulfate, clarified and taken to dryness under vacuum. The crude reaction mixture was crystallized from chloroform yielding 26.2 g of analytically pure product mp 99°–101° C.

EXAMPLE 10

1-Phenyl-1-propynyl-2-(3-sulfamoyl-4-chlorobenzoyl)-hydrazine

In a three necked 1 liter round bottom reaction vessel equipped with a mechanical stirrer and reflux condenser were placed 97.5 g (0.3 mol) of the compound of Example 8 and 200 ml of hexamethylphosphoric-triamide. The mixture was heating with stirring under nitrogen at 80°–90° C. till the solid dissolved. To this solution was added with stirring 252 g (3 mol) sodium bicarbonate powder. Over a period of about 0.5 hour 29.4 ml of an 80% w/w solution of propargyl bromide in toluene (0.315 mol propargyl bromide) were added with stirring. After the reaction had run for 21 hours an additional 4 ml of the propargyl bromide solution in toluene (0.043 mol propargyl bromide) was added and the reaction continued for an additional 68 hours. The reaction mixture was then cooled and diluted with 1 liter of ethyl acetate. The mixture was transferred to a separatory funnel, cross-washed with water/brine, then with a 2 molor aqueous citric acid and again with brine. The organic layer was dried over anhydrous magnesium sulfate, clarified and evaporated to yield 108 g of a dark oil which was purified by chromatography over silica gel to yield a solid which was recrystallized from ethyl acetate/hexane. M.p. 168°–170° C.

EXAMPLE 11

1-Allyl-1-phenyl-2-(3-sulfamoyl-4-chlorobenzoyl)-hydrazine

1-Phenyl-2-(3-sulfamoyl-4-chlorobenzoyl)-hydrazine 5 g (0.015 mol) was dissolved in dimethylformamide (15 ml). To this was added allyl bromide 2.8 g (0.023 mol) and the mixture was heated at 95°–100° C. for about 1.5 hours. The reaction mixture was cooled and diluted with 30 ml of isopropanol and added slowly to about 900 ml of cold water. The precipitate was collected by filtration, washed with water and dried under reduced pressure to provide 1-allyl-1-phenyl-2-(3-sulfamoyl-4-chlorobenzoyl)-hydrazine (m.p. 99°–101° C.).

EXAMPLE 12

1-Allyl-1-phenyl-2-(3-sulfamoyl-4-chlorobenzoyl)-hydrazine

In a three necked 12 liter round bottom reaction flask equipped with a mechanical stirrer and reflux condenser was placed isopropanol 6.1 liters and 1-phenyl-2-(3-sulfamoyl-4-chlorobenzoyl)-hydrazine 1.3 kg (4.1 mol), potassium iodide 68.0 g (0.41 mol) and allyl bromide 768 g (8 mol). This mixture was stirred at gentle reflux for about 20 hours then suction filtered while still hot. The cake was washed with isopropanol 300 ml and the combined filtrate and wash were diluted with warm water 2.7 liters. Crystallization occured in about 0.5 hours. The crystals were filtered and washed with isopropanol-water (70% v/v) to provide the compound (m.p. 99°–101° C.).

EXAMPLE 13

1-Phenyl-1-propynyl-2-(3-sulfamoyl-4-chlorobenzoyl)-hydrazine

1-Phenyl-2-(3-sulfamoyl-4-chlorobenzoyl)-hydrazine 5 g (0.015 mol) was dissolved in dimethylformamide (20 ml). To this was added propargyl bromide 3.6 g (0.03 mol) and the mixture heated at 95°–100° C. for about 2 hours. The reaction mixture was concentrated under reduced pressure at about 40°–45° C. on a rotary evaporator. The concentrate was then diluted with approximately 2 volumes of isopropanol and added slowly to about 600 ml of vigorously stirred water. The precipitate was collected by filtration, washed with water and dried under reduced pressure to provide 1-phenyl-1-propynyl-2-(3-sulphamoyl-4-chlorobenzoyl)-hydrazine (m.p. 168°–170° C.).

Using the procedures in the above examples compounds wherein $R_1$ was hydroxy, alkyl, alkoxy, nitro, halo, amino, trifluoro-methyl mercapto and alkyl mercapto, and $R_2$ and $R_3$ were alkyl, cycloalkyl and alkenyl can be prepared. Where $R_1$ is hydroxy, amino or mercapto the group is protected in the usual manner prior to the reaction with the sulfamoyl halobenzoyl halide and the protective group removed after the reaction.

By following the procedures in the above examples the following additional compounds may be prepared:

2-[(4-chloro-3-sulfamoyl)-benzoyl]-1-crotyl-1-phenyl-hydrazine,

2-[(4-chloro-3-sulfamoyl)-benzoyl]-1-(2-butynyl)-1-phenyl-hydrazine,

2-[(4-chloro-3-sulfamoyl)-benzoyl]-1]-(3-methyl-2-butenyl)-1-phenyl-hydrazine,

2-[(4-chloro-3-sulfamoyl)-benzoyl]-1-phenyl-1-cyclopropyl-methylhydrazine,

2-[(4-chloro-3-sulfamoyl)-benzoyl]-1-phenyl-1-cyclopentyl-methylhydrazine,

2-[(4-chloro-3-sulfamoyl)-benzoyl]-1-phenyl-1-cyclobutyl-methylhydrazine,

2-[(4-chloro-3-sulfamoyl)-benzoyl]-1-(2,6-dichlorophenyl)-1-cyclopropyl methyl hydrazine, and 2-](4-chloro-3-sulfamoyl)-benzoyl]-2-methyll phenyl-1-allyl-hydrazine.

The compounds of the present invention exhibited antihypertensive and diuretic activities which would make them useful in the treatment of hypertension. In particular, the compounds, 1-allyl-1-phenyl-2-(3-sulfamoyl-4-chlorobenzoyl)-hydrazine and 1-propargyl-1-phenyl-2-(3-sulfamoyl-4-chlorobenzyl)-hydrazine, showed both potent diuretic and antihypertensive activities in rats and other mammals. In spontaneously hypertensive rats, 1-allyl-1-phenyl-2-(3-sulfamoyl-4-chlorobenzoyl)-hydrazine exhibited an antihypertensive $ED_{50}$ in the rat of 3 mg/kg i.p. and 30 mg/kg p.o.

The compounds may be mixed with solid or liquid pharmaceutical carriers and formulated into tablets, powders or capsules for oral administration or dissolved in suitable solvents for either oral or parental administration.

We claim:

1. A compound of the formula

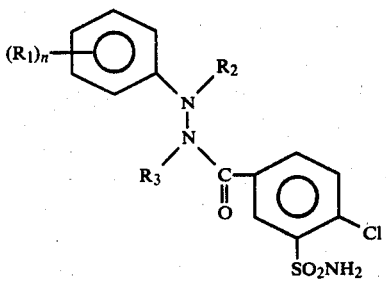

wherein
- $R_1$ is independently halogen, lower alkyl or trifluoromethyl,
- n is an integer from 0 to 2,
- $R_2$ is lower alkenyl, lower alkynyl, or cycloalkyl, and
- $R_3$ is hydrogen or lower alkyl wherein
the alkyl, alkenyl, and alkynyl groups contain up to 6 carbon atoms and the cycloalkyl groups contain from 3 to 7 carbon atoms.

2. A compound according to claim 1 wherein n is 0.

3. A compound according to claim 2 wherein $R_2$ is allyl and $R_3$ is hydrogen.

4. A compound according to claim 2 wherein $R_2$ is propargyl and $R_3$ is hydrogen.

5. A compound according to claim 2 wherein $R_2$ is cyclopropylmethyl and $R_3$ is hydrogen.

6. A compound according to claim 2 wherein $R_2$ is allyl and $R_3$ is methyl.

7. A compound according to claim 2 wherein $R_2$ is $CH_3C{\equiv}C{-}CH_2{-}$ and $R_3$ is hydrogen.

8. A compound according to claim 2 wherein $R_2$ is $(H_3C)C{=}C(CH_3){-}CH_2{-}$ and $R_3$ is hydrogen.

9. A method of treating hypertension which comprises administering to animals having hypertension an effective dose of a compound of claim 1.

* * * * *